United States Patent [19]

Sassin

[11] Patent Number: 5,300,089
[45] Date of Patent: Apr. 5, 1994

[54] INFANT PACIFIER CONSTRUCTION

[76] Inventor: Susan J. Sassin, 21601 Poinciana, Southfield, Mich. 48034

[21] Appl. No.: 31,708

[22] Filed: Mar. 15, 1993

[51] Int. Cl.⁵ .......................... A61M 31/00; A61J 7/00
[52] U.S. Cl. ..................................... 606/236; 606/234; D24/196
[58] Field of Search .............................. 215/11.1–11.6; 606/234–236; D24/194–199

[56] References Cited

U.S. PATENT DOCUMENTS

| | | | |
|---|---|---|---|
| 1,122,306 | 12/1914 | Reschke | 606/236 |
| 2,889,829 | 6/1959 | Tannenbaum et al. | 606/236 |
| 5,013,321 | 5/1991 | MacVane | 606/234 |
| 5,078,734 | 1/1992 | Noble | 606/234 |
| 5,123,915 | 6/1992 | Miller et al. | 606/234 |
| 5,127,903 | 7/1992 | Mailot et al. | 606/236 |
| 5,176,705 | 1/1993 | Noble | 606/236 |

Primary Examiner—Stephen C. Pellegrino
Assistant Examiner—Glenn K. Dawson
Attorney, Agent, or Firm—Leon Gilden

[57] ABSTRACT

A pacifier is arranged to include a base disc mounting a base plug, wherein the base plug is directed through the base disc mounting a nipple head. The nipple head defines an annular groove between the nipple head and the base plug at a front wall of the base disc to enhance grasping of the nipple by an infant, wherein the nipple head includes a first inwardly tapered base portion extending from the annular base directed to a second outwardly tapered base portion, in turn directed to a third inwardly tapered base portion that in turn is directed into a nipple head tip, wherein the nipple head is canted from the annular base towards the nipple head tip defining an undulating outer surface for enhanced grasping by an infant in use. The nipple head is arranged to include a cavity to contain a fluid or freezable gel to enhance soothing use by the infant. A modification of the invention is directed to the fluid accessed to the infant and replenished through an access plug directed through the base plug.

4 Claims, 4 Drawing Sheets

INFANT PACIFIER CONSTRUCTION

BACKGROUND OF THE INVENTION

1. Field of the Invention

The field of invention relates to pacifier construction, and more particularly pertains to a new and improved infant pacifier construction arranged to a simulate human breast portion for efficient and soothing use by an infant.

2. Description of the Prior Art

Pacifier construction of various types have been utilized throughout the prior art such as typified in the U.S. Pat. Nos. 4,909,253; 4,796,628; 4,697,589; and 4,898,171.

The instant invention attempts to overcome deficiencies of the prior art by providing for a pacifier construction arranged to simulate a human breast in use and in this respect, the present invention substantially fulfills this need.

SUMMARY OF THE INVENTION

In view of the foregoing disadvantages inherent in the known types of pacifier construction now present in the prior art, the present invention provides an infant pacifier construction wherein the same is directed to a pacifier employing a nipple head including an outwardly projected and tapered head portion for enhanced simulation of a human breast in use. As such, the general purpose of the present invention, which will be described subsequently in greater detail, is to provide a new and improved infant pacifier construction which has all the advantages of the prior art pacifier construction and none of the disadvantages.

To attain this, the present invention provides a pacifier arranged to include a base disc mounting a base plug, wherein the base plug is directed through the base disc mounting a nipple head. The nipple head defines an annular groove between the nipple head and the base plug at a front wall of the base disc to enhance grasping of the nipple by an infant, wherein the nipple head includes a first inwardly tapered base portion extending from the annular base directed to a second outwardly tapered base portion, in turn directed to a third inwardly tapered base portion that in turn is directed into a nipple head tip, wherein the nipple head is canted from the annular base towards the nipple head tip defining an undulating outer surface for enhanced grasping by an infant in use. The nipple head is arranged to include a cavity to contain a fluid or freezable gel to enhance soothing use by the infant. A modification of the invention is directed to the fluid accessed to the infant and replenished through an access plug directed through the base plug.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved infant pacifier construction which has all the advantages of the prior art pacifier construction and none of the disadvantages.

It is another object of the present invention to provide a new and improved infant pacifier construction which may be easily and efficiently manufactured and marketed.

It is a further object of the present invention to provide a new and improved infant pacifier construction which is of a durable and reliable construction.

An even further object of the present invention is to provide a new and improved infant pacifier construction which is susceptible of a low cost of manufacture with regard to both materials and labor, and which accordingly is then susceptible of low prices of sale to the consuming public, thereby making such infant pacifier construction economically available to the buying public.

Still yet another object of the present invention is to provide a new and improved infant pacifier construction which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
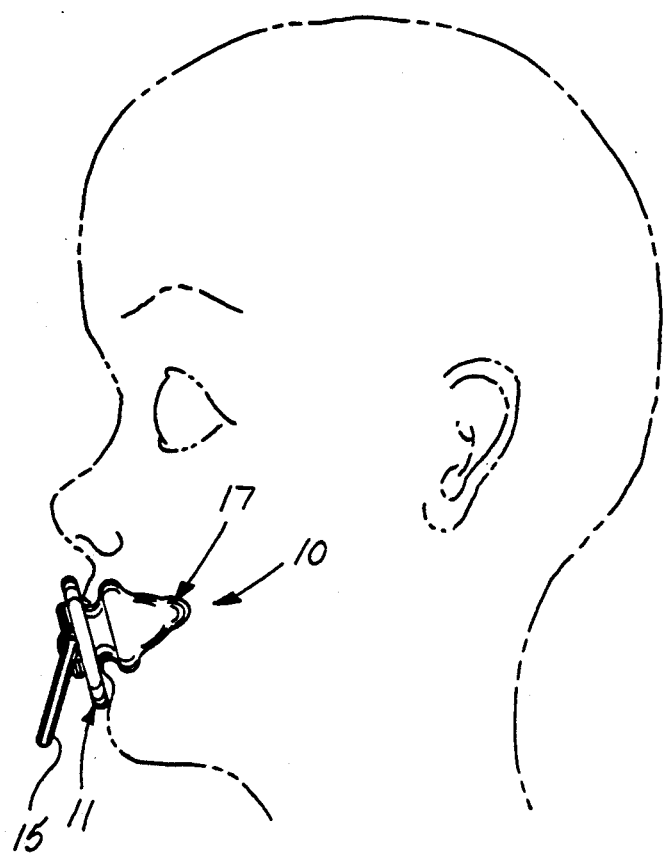
FIG. 1 is an orthographic side view of the invention in use.
Figure 2:
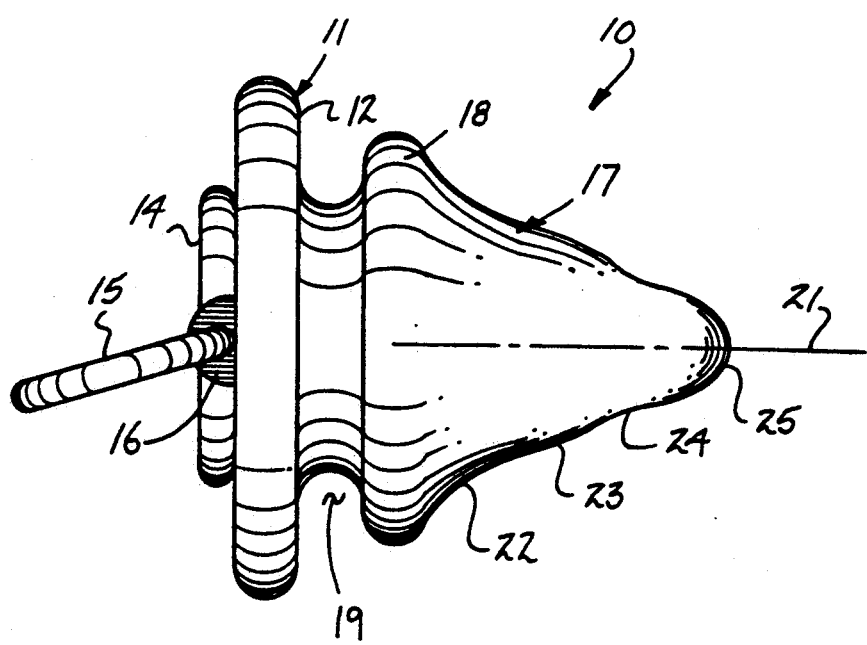
FIG. 2 is an enlarged orthographic side view of the invention.

With reference now to the drawings, and in particular to FIGS. 1 to 9 thereof, a new and improved infant pacifier construction embodying the principles and concepts of the present invention and generally designated by the reference numerals 10 and 10a will be described.

More specifically, the infant pacifier construction 10 of the instant invention, as indicated in the FIGS. 1-4, indicates the use of a resilient base disc 11, having a front wall 12 spaced from a rear wall 13 in a parallel coextensive relationship. A base plug 14 is directed orthogonally and through the base disc projecting from the rear wall 13 through the front wall 12 mounting a nipple head 17 in a spaced relationship relative to the front wall 12. A support loop 15 is provided pivotally mounted to the rear wall 13 about anchor lugs 16 that are positioned on diametrically opposed sides of the rear wall 13, as indicated in the FIGS. 1 and 4 for example. The nipple head 17 includes an annular base 18, wherein an annular groove 19 is defined between the annular base 18 and the front wall 12 to enhance grasping of the nipple, in a manner as indicated in FIG. 1, by an infant. The annular base 18 tapers in an undulating manner towards a nipple head tip 25. It is understood that the pacifier 10 is symmetrically oriented about a central axis 21 relative to the various components thereof as described. A first inwardly tapering head portion 22 extends from the annular base 18 towards the tip, wherein a second outwardly tapering head portion 23 tapers outwardly relative to the central axis 21 of the first head portion 22, wherein a third inwardly tapering head portion 24 extends from the second outwardly tapering head portion 23 towards the nipple head tip 25. In this manner, simulation of human anatomy, as well as enhanced grasping of the pacifier structure in use is effected.

Figure 3:
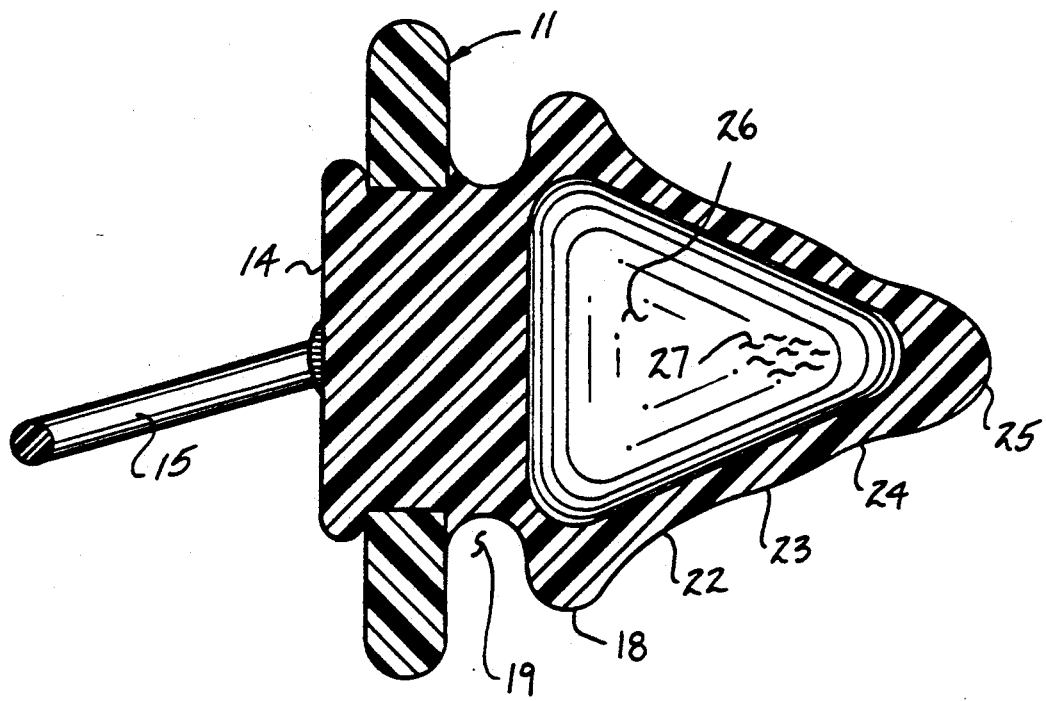
FIG. 3 is an orthographic cross-sectional illustration of the invention.
Figure 4:
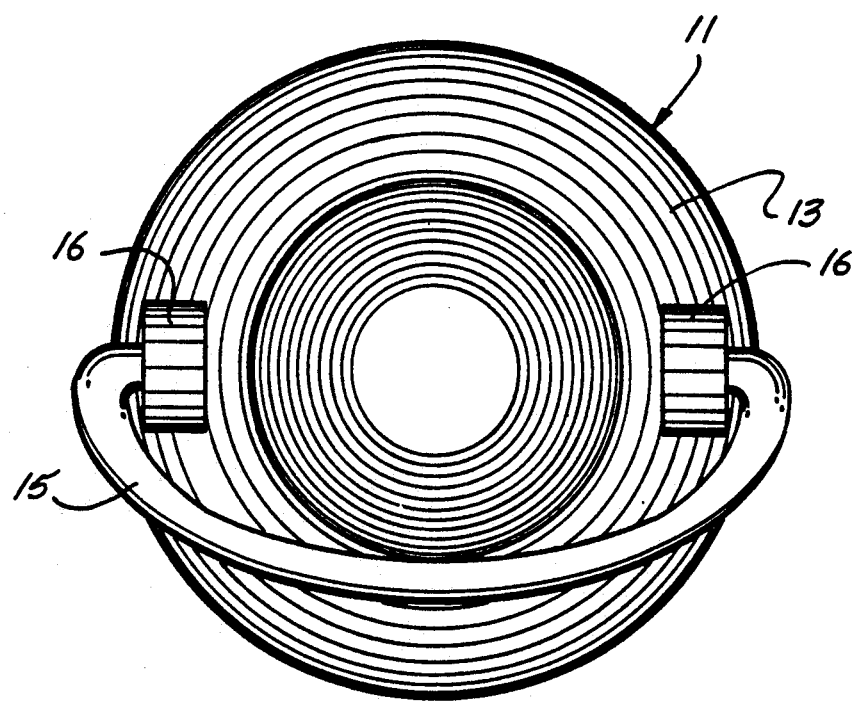
FIG. 4 is an orthographic end view of the invention.
Figure 5:
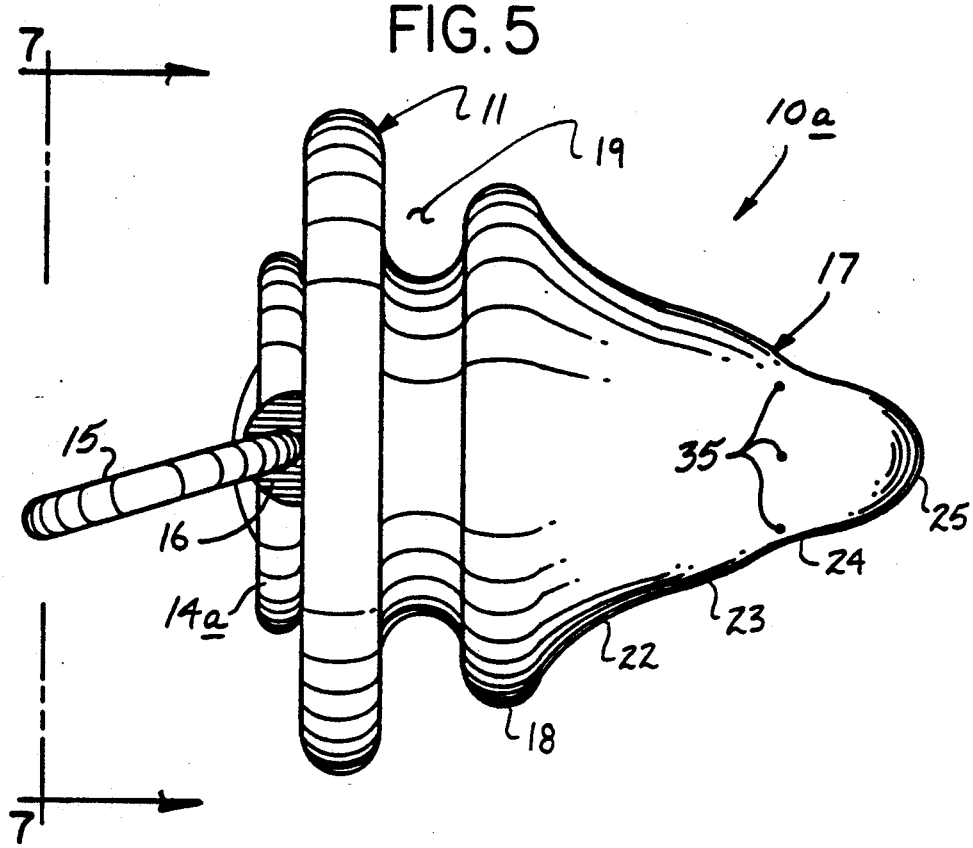
FIG. 5 is an orthographic side view of a modified aspect of the invention.
Figure 6:
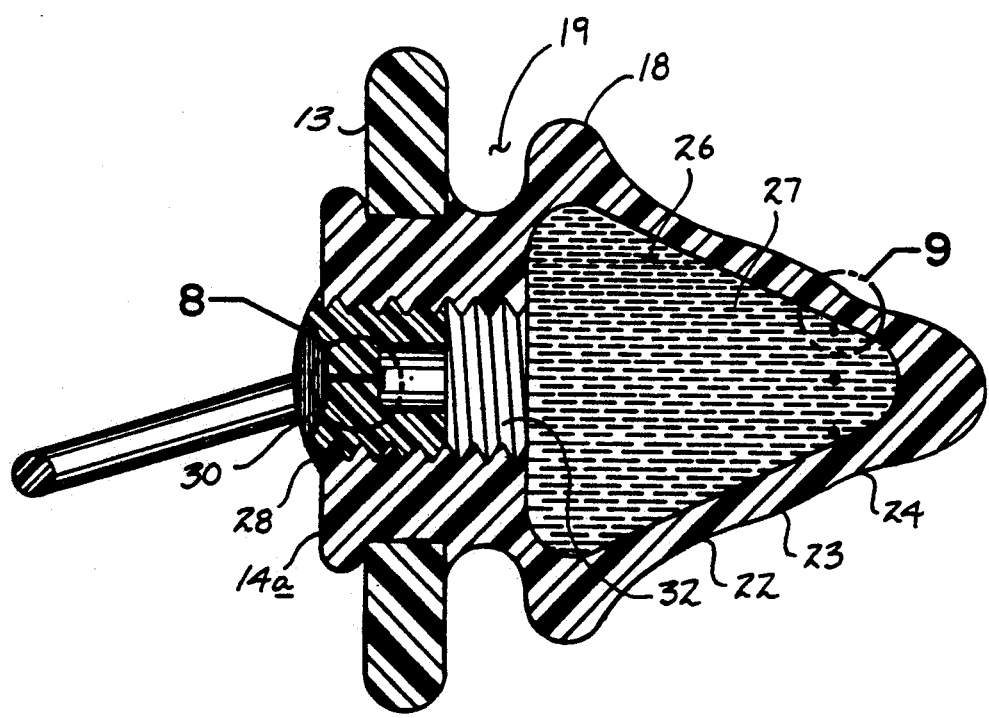
FIG. 6 is an orthographic cross-sectional illustration of the invention, as indicated in FIG. 5.
Figure 7:
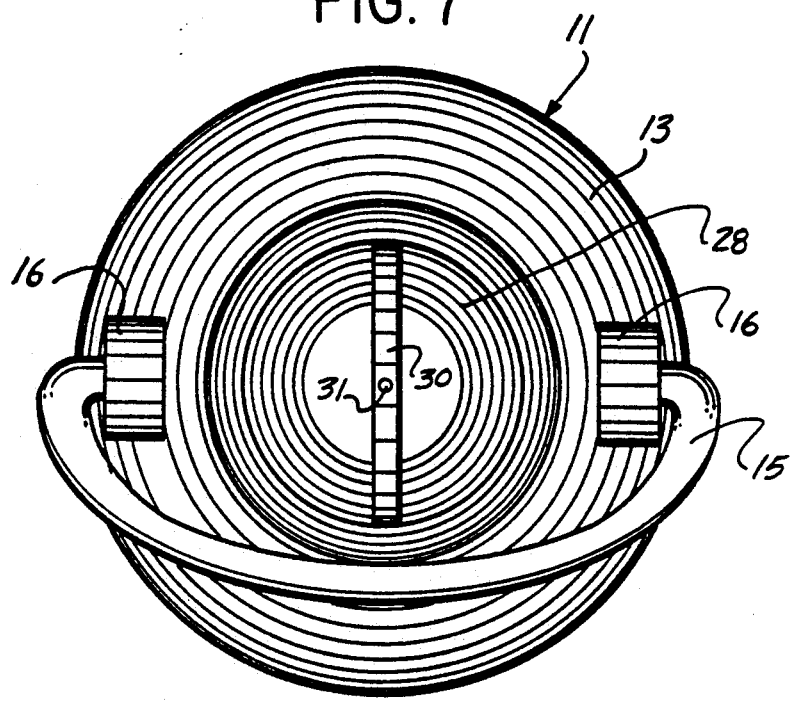
FIG. 7 is an orthographic view, taken along the lines 7—7 of FIG. 6 in the direction indicated by the arrows.
Figure 8:
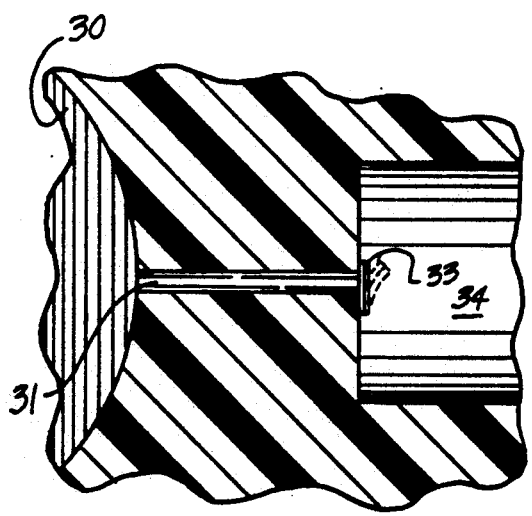
FIG. 8 is an enlarged orthographic view of section 8 as set forth in FIG. 6.
Figure 9:
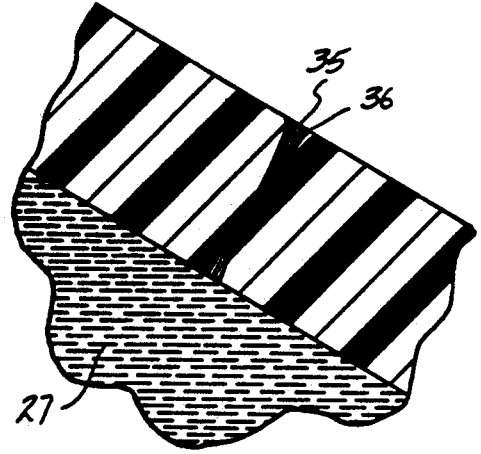
FIG. 9 is an enlarged orthographic view of section 9 as set forth in FIG. 6.

Reference to FIG. 3 indicates the use of a head fluid cavity 26 positioned within the head extending from the plug 14 to the tip 25 containing a fluid 27 or a freezable gel therewithin.

Reference to the FIGS. 5-9 indicates a modified infant pacifier construction 10a, wherein in addition to the structure as noted above, an externally threaded access plug 28 is threadedly received within a base plug internally threaded bore 32 coaxially directed through a modified base plug 14a. The access plug 28 includes a slot 30 directed into the access plug for ease of disassembling the access plug relative to the threaded bore 32 by use of a screwdriver and the like. A vent conduit 31 coincident with the central axis 21 is directed from the slot 30 into an interior port 34, that in turn is in communication with the base plug internally threaded bore 32, that in turn is in communication with the head fluid cavity 26. The vent conduit 31 (see FIG. 8) includes a resilient check valve plate 33 hingedly mounted within the interior port 34, whereupon suction directed through the vent conduit 31 displaces the resilient check valve plate 33 from the vent conduit 31 within the interior port 34, whereupon absence of suction by an infant through the head fluid cavity 26 releases the check valve plate 33 to again effect closure of the vent conduit 31 relative to the interior port 34.

An annular array of suction conduits 35 are directed through the nipple head 17 at the third inwardly tapered head portion 24. Each of the suction conduits 35 in communication with the head fluid cavity 26 permits the drawing of suction through the fluid cavity 26, wherein preventing undesired weepage of fluid through the suction conduits 35, each of the suction conduits 35 is formed with resiliently biased conduit wall 36 that is closed upon the absence of suction but is displaced in a second position from the first closed position upon directing of suction through the suction conduits 35 by an infant. In this manner, fluid 27 contained within the cavity 26 is accessed through the suction conduits 35 by an infant in use and vented through the vent conduit 31.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An infant pacifier construction, comprising,
   a resilient base disc, having a front wall spaced from, parallel to, and coextensive with a rear wall, and
   a base plug directed through the base disc, with the base plug projecting beyond the front wall, and
   a nipple head fixedly mounted to the base plug, with the head arranged in a spaced relationship relative to the base disc, wherein the base disc, the base plug, and the nipple head are coaxially aligned along a central axis, and
   the base plug including an annular groove between the nipple head and the front wall, and
   the nipple head includes an annular base, and a nipple head tip, wherein the nipple head is undulating from the annular base to the nipple head tip, and wherein a first inwardly tapered head portion extends from the annular base towards the central axis, and a second outwardly tapered head portion extending from the first inwardly tapered head portion exteriorly of the central axis, and a third inwardly tapered head portion extends from the second outwardly tapered head portion towards the central axis and the nipple head tip, and a fluid cavity positioned within the nipple head between the base plug and the nipple head tip, with a fluid contained within the fluid cavity, and the base plug includes a base plug internally threaded bore, and an externally threaded access plug threadedly received within the base plug internally threaded bore, and a slot directed into the access plug, with a vent conduit directed from the slot through the access plug.

2. A pacifier construction as set forth in claim 1 wherein an interior port is positioned within the access plug in communication with the fluid cavity, and the vent conduit is in communication with the interior port, and a resilient check valve plate hingedly mounted within the interior port arranged to extend over the vent conduit within the interior port in a first position, with the resilient check valve plate displaced from the vent conduit in a second position upon suction being directed to the vent conduit through the fluid cavity.

3. A pacifier construction as set forth in claim 1 wherein an annular array of suction conduits are directed through the nipple head in communication with the fluid cavity, with the suction conduits directed into the third inwardly tapered head portion.

4. A pacifier construction as set forth in claim 3 wherein each of the suction conduits includes a resiliently biased conduit wall closed in a first position and opened in a second position upon suction being directed through the suction conduits.

* * * * *